United States Patent
Tung et al.

(10) Patent No.: US 8,084,653 B2
(45) Date of Patent: *Dec. 27, 2011

(54) METHOD FOR PRODUCING FLUORINATED ORGANIC COMPOUNDS

(75) Inventors: Hsueh S. Tung, Getzville, NY (US); Sudip Mukhopadhyay, Williamsville, NY (US); Michael Van Der Puy, Amherst, NY (US); Daniel C. Merkel, West Seneca, NY (US); Jing Ji Ma, West Seneca, NY (US); Cheryl L. Bortz, N. Tonawanda, NY (US); Barbara A. Light, Niagara Falls, NY (US); Steven D. Phillips, New York, NY (US); Rajesh K. Dubey, Williamsville, NY (US)

(73) Assignee: Honeywell International, Inc., Morristown, NJ (US)

( * ) Notice: Subject to any disclaimer, the term of this patent is extended or adjusted under 35 U.S.C. 154(b) by 1391 days.

This patent is subject to a terminal disclaimer.

(21) Appl. No.: 11/619,592

(22) Filed: Jan. 3, 2007

(65) Prior Publication Data
US 2007/0197842 A1 Aug. 23, 2007

Related U.S. Application Data

(63) Continuation-in-part of application No. 11/118,504, filed on Apr. 29, 2005, now Pat. No. 7,371,904, which is a continuation-in-part of application No. 11/118,503, filed on Apr. 29, 2005, now Pat. No. 7,345,209, which is a continuation-in-part of application No. 11/118,530, filed on Apr. 29, 2005, now Pat. No. 7,189,884.

(60) Provisional application No. 60/755,485, filed on Jan. 3, 2006, provisional application No. 60/567,426, filed on Apr. 29, 2004, provisional application No. 60/567,429, filed on Apr. 29, 2004, provisional application No. 60/567,427, filed on Apr. 29, 2004, provisional application No. 60/567,425, filed on Apr. 29, 2004, provisional application No. 60/567,428, filed on Apr. 29, 2004.

(51) Int. Cl.
*C07C 17/00* (2006.01)
*C07C 19/08* (2006.01)
*C07C 21/18* (2006.01)
*C07C 23/00* (2006.01)
*C07C 25/13* (2006.01)
(52) U.S. Cl. ........................................................ 570/123
(58) Field of Classification Search .................. None
See application file for complete search history.

(56) References Cited

U.S. PATENT DOCUMENTS

| | | | |
|---|---|---|---|
| 2,931,840 A | 4/1960 | Marquis .................... 260/653.3 |
| 2,996,555 A | 8/1961 | Rausch et al. |
| 3,472,826 A | 10/1969 | Potts et al. |
| 3,659,023 A | 4/1972 | Regan |
| 4,086,407 A | 4/1978 | Fozzard ............................ 526/75 |
| 4,650,914 A | 3/1987 | Woodard et al. |
| 4,798,818 A | 1/1989 | Baizer et al. |
| 4,900,874 A | 2/1990 | Ihara et al. |
| 5,532,419 A | 7/1996 | Vand Der Puy et al. |
| 5,545,777 A | 8/1996 | Morikawa et al. |
| 5,574,192 A | 11/1996 | Van Der Puy et al. |
| 5,679,875 A | 10/1997 | Aoyama et al. |
| 5,986,151 A | 11/1999 | Van Der Puy et al. |
| 6,111,150 A | 8/2000 | Sakyu et al. |
| 6,124,510 A | 9/2000 | Elsheik et al. |
| 6,369,284 B1 | 4/2002 | Nappa et al. |
| 6,548,719 B1 | 4/2003 | Nair et al. |
| 6,809,226 B1 | 10/2004 | Pennetreau et al. |
| 6,958,424 B1 | 10/2005 | Nair et al. |
| 7,189,884 B2 * | 3/2007 | Mukhopadhyay et al. ... 570/160 |
| 7,230,146 B2 * | 6/2007 | Merkel et al. ................. 570/155 |
| 7,659,434 B2 * | 2/2010 | Mukhopadhyay et al. ... 570/136 |
| 7,674,939 B2 * | 3/2010 | Mukhopadhyay et al. ... 570/156 |
| 7,700,815 B2 * | 4/2010 | Tung et al. .................... 570/153 |
| 2003/0060670 A1 | 3/2003 | Nair et al. ....................... 570/155 |

(Continued)

FOREIGN PATENT DOCUMENTS
EP 522639 1/1993
(Continued)

OTHER PUBLICATIONS

U.S. Appl. No. 12/702,135, filed Feb. 2010, Mukhopadhyay et al.*
Henne, Albert L. et al; Fluorinated derivatives of propane and propylene; vol. 68; p. 496-497; 1946; XP002448570.
Paleta, Oldrich et al; Synthesis of perfluoroallyl chloride and some chlorofluoropropenes; No. 6; p. 920-924; 1986; XP009088473.

(Continued)

*Primary Examiner* — Daniel Sullivan
*Assistant Examiner* — Clinton Brooks
(74) *Attorney, Agent, or Firm* — Bruce Bradford

(57) ABSTRACT

Disclosed are processes for the production of fluorinated olefins, preferably adapted to commercialization of $CF_3CF=CH_2$ (1234yf). Three steps may be used in preferred embodiments in which a feedstock such as $CCl_2=CClCH_2Cl$ (which may be purchased or synthesized from 1,2,3-trichloropropane) is fluorinated (preferably with HF in gas-phase in the presence of a catalyst) to synthesize a compound such as $CF_3CCl=CH_2$, preferably in a 80-96% selectivity. The $CF_3CCl=CH_2$ is preferably converted to $CF_3CFClCH_3$ (244-isomer) using a $SbCl_5$ as the catalyst which is then transformed selectively to 1234yf, preferably in a gas-phase catalytic reaction using activated carbon as the catalyst. For the first step, a mixture of $Cr_2O_3$ and $FeCl_3/C$ is preferably used as the catalyst to achieve high selectivity to $CF_3CCl=CH_2$ (96%). In the second step, $SbCl_5/C$ is preferably used as the selective catalyst for transforming 1233xf to 244-isomer, $CF_3CFClCH_3$. The intermediates are preferably isolated and purified by distillation and used in the next step without further purification, preferably to a purity level of greater than about 95%.

41 Claims, No Drawings

U.S. PATENT DOCUMENTS

| | | |
|---|---|---|
| 2005/0020862 A1 | 1/2005 | Tung et al. |
| 2005/0080302 A1 | 4/2005 | Baker et al. |
| 2005/0090698 A1* | 4/2005 | Merkel et al. ............ 570/155 |
| 2005/0171391 A1 | 8/2005 | Janssens et al. |
| 2009/0030245 A1* | 1/2009 | Ma et al. .................. 570/136 |
| 2009/0099396 A1* | 4/2009 | Mukhopadhyay et al. ... 570/160 |

FOREIGN PATENT DOCUMENTS

| | | |
|---|---|---|
| EP | 0522639 | 1/1993 |
| JP | 11140002 | 5/1999 |
| JP | 2000169404 | 6/2000 |
| WO | WO 9504021 | 2/1995 |
| WO | WO/96/01797 A | 1/1996 |
| WO | WO 98/21171 | 5/1998 |
| WO | WO 01/07384 | 2/2001 |
| WO | WO2005/042451 A | 5/2005 |

OTHER PUBLICATIONS

Maria O. Burgin et al; Unimolecular reaction kinetics of CF2CLCF2CH3 and CF2CLCF2CD3; vol. 105, p. 1615-1621; 2001 XP002448571.

U.S. Appl. No. 10/694,273, filed Oct. 27, 2003, Singh et al.

Zhuranl Organicheskoi Khimii, 28(4), 672-80, (1982).

Free-radical additions to unsaturated systems, Journal of Chemical Society, Section C: Organic, (3), 414-21, p. 415, 1970.

* cited by examiner

METHOD FOR PRODUCING FLUORINATED ORGANIC COMPOUNDS

CROSS-REFERENCES TO RELATED APPLICATIONS

This application is related to and claims the priority benefit of U.S. provisional application No. 60/755485, filed Jan. 3, 2006.

This application is also a Continuation-in-Part of U.S. patent application Ser. No. 11/118,503, (pending) filed on Apr. 29, 2005, which in turn claims the priority benefit of U.S. Provisional Patent Application Nos. 60/567,427 and 60/567,425 filed Apr. 16, 2004.

This application is also a Continuation-in-Part of U.S. patent application Ser. No. 11/118,504, (pending) filed on Apr. 29, 2005, which in turn claims the priority benefit of U.S. Provisional Patent Application Nos. 60/567,426 and 60/567,429 filed Apr. 16, 2004.

This application is also a Continuation-in-Part of U.S. patent application Ser. No. 11/118,530, (pending) filed on Apr. 29, 2005, which in turn claims the priority benefit of U.S. Provisional Patent Application No. 60/567,428.

The disclosures of each of the above-mentioned applications are incorporated herein by reference. Also incorporated herein by reference are the following U.S. Applications 60/733,378; 60/733,444; 60/733383; 60/733,355 and 60/733,379 each of which was filed on Nov. 3, 2005.

BACKGROUND OF INVENTION (1) Field of Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such tetrafluoropropenes (including 2,3,3,3-tetrafluoro-1-propene (HFO-1234yf) and 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkenes are known. For example, U.S. Pat. No. 4,900,874 (Ihara et al) describes a method of making fluorine containing olefins by contacting hydrogen gas with fluorinated alcohols. Although this appears to be a relatively high-yield process, for commercial scale production the handling of hydrogen gas at high temperature raises difficult safety related questions. Also, the cost of producing hydrogen gas, such as building an on-site hydrogen plant, can be in many situations prohibitive.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted in this process to unwanted and/or unimportant byproducts.

The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

SUMMARY

Applicants have discovered a method for producing fluorinated organic compounds, including hydrofluoropropenes, which preferably comprises converting at least one compound of Formula (I):

$$C(X)_mCCl(Y)_nC(X)_m \qquad (I)$$

to at least one compound of Formula (II)

$$CF_3CF=CHZ \qquad (II)$$

where each X, Y and Z is independently H, F, Cl, I or Br, and each m is independently 1, 2 or 3, and n is 0 or 1. As used herein and throughout, unless specifically indicated otherwise, the term "converting" includes directly converting (for example, in a single reaction or under essentially one set of reaction conditions, an example of which is described hereinafter) and indirectly converting (for example, through two or more reactions or using more than a single set of reaction conditions).

In certain preferred embodiments of the invention, the compound of Formula (I) comprises a compound wherein n is 0, each X is independently H or Cl, and Z is H. Such preferred embodiments include converting at least one C3 alkene in accordance with Formula (IA):

$$C(X)_2=CClC(X)_3 \qquad (IA)$$

to at least one compound of formula (II)

$$CF_3CF=CHZ \qquad (II)$$

where each X is independently H or Cl. Preferably the one or more compounds of Formula (IA) are tetrachloropropene(s), and are even more preferably selected from the group consisting of $CH_2=CClCCl_3$, $CCl_2=CClCH_2Cl$, $CHCl=CClCCl_2H$, and combinations of these.

In certain preferred embodiments of the invention the compound of Formula (I) comprises a compound wherein n is 0 and the terminal saturated carbon has three (3) F substituents. Such preferred embodiments include converting at least one C3 alkene in accordance with Formula (IAA):

$$C(X)_2=CClCF_3 \qquad (IAA)$$

to at least one compound of formula (II)

$$CF_3CF=CHZ \qquad (II)$$

where each X is independently H or Cl. Preferably the one or more compounds of Formula (IAA) are trifluoropropene(s). Included in the preferred trifluorpropene compounds of the present invention is $CH_2=CClCF_3$ (HCFC-1223xf).

In certain preferred embodiments the compound of Formula (I) comprises a compound wherein n is 1 and each X and Y is independently H, F or Cl. Such embodiments include converting at least one C3 alkane of Formula (IB):

$$C(X)_3CClYC(X)_3 \qquad (IB)$$

to at least one compound of formula (II)

$$CF_3CF=CHZ \qquad (II)$$

where each X and Y is independently H, F or Cl. In certain preferred embodiments, the Formula (IB) compound has at least two haologens on one terminal carbon and at least two hydrogen atoms on the other terminal carbon. Preferably the compounds of Formula (IB) contain at least four halogen substituents and even more preferably at least five halogen substituents. In certainly highly preferred embodiments, the conversion step of the present invention comprises converting a compound of Formula (IB) wherein Y is F and all three X on one terminal carbon are F. Preferably the compound of Formula (IB) is a penta-halogenated propane, preferably with at least four fluorine substituents. Even more preferably the penta-halogenated propane of Formula (IB) comprises a tetra-fluorinated, mono-chlorinated propane, including chlorotetrafluoropropane ($C_3H_3F_4Cl$), including all isomers thereof, such as 1,1,1,2-tetrafluoro-2-chloropropane and 1-chloro-1,3,3,3-tetrafluoropropane (HFC-244fa). Other preferred penta-halogenated compounds of Formula (IB) include $CH_2ClCHClCCl_3$, $CHCl_2CCl_2CH_2Cl$, $CHCl_2CHClCHCl_2$. Of course, combinations of compounds of Formula (I), including combinations of compounds of Formulas (IA), (IAA) and (IB) may be used.

In certain preferred embodiments, the step of converting a compound of Formula (I) to at least one compound of Formula (II) comprises directly converting a compound of Formula (I). In other embodiments, the step of converting a compound of Formula (I) to at least one compound of Formula (II) comprises indirectly converting a compound of Formula (I).

An example of indirect conversion embodiments includes converting a compound of Formula (IA) to a compound of Formula (IAA), then converting said Formula (IAA) compound to a Formula (IB) compound, and then converting the Formula (IB) to the Formula (II) compound. In certain more specific indirect conversion embodiments, the step of converting a compound of Formula (I) comprises providing at least one monchlortrifluorpropene in accordance with Formula (IAA), preferably $CF_3CCl\!=\!CH_2$ (HFO-1233xf) and reacting said monchlortrifluorpropene under conditions effective to produce at least one monchlortetrafluorpropane in accordance with Formula (IB), preferably $CF_3CFClCH_3$ (HFC-244bb), which in turn is preferably exposed to reaction conditions effective to produce at least one compound in accordance with Formula (II), preferably HFO-1234yf. In preferred embodiments said exposing step comprises conducting one or more of said reactions in a gas phase in the presence of a catalyst, preferably a metal-based catalyst. Examples of such preferred conversion steps are disclosed more fully hereinafter. Of course, it is contemplated that in the broad scope of the invention that any of the Formula (I) compounds may be converted, directly or indirectly, to a compound of Formula (II) in view of the teachings contained herein.

In certain preferred embodiments the converting step comprises exposing the compound of Formula (I), and preferably Formula (1A), (IAA) or Formula (1B), to one or more sets of reaction conditions effective to produce at least one compound in accordance with Formula (II). It is contemplated that in certain embodiments the exposing step comprises reacting said one or more compound(s) of Formula (IA) or (IAA) under conditions effective to produce chlorofluoropropane, more preferably a propane in accordance with Formula (IBB):

$CF_3CClFC(X)_3$  Formula (IBB)

where each X is independently F, Cl or H. In certain preferred embodiments, at least one of said X in Formula (IBB) is H, and even more preferably all three X are H.

The preferred conversion step of the present invention is preferably carried out under conditions, including the use of one or more reactions, effective to provide a Formula (I) conversion of at least about 50%, more preferably at least about 75%, and even more preferably at least about 90%. In certain preferred embodiments the conversion is at least about 95%, and more preferably at least about 97%. Further in certain preferred embodiments, the step of converting the compound of Formula (I) to produce a compound of Formula (II) is conducted under conditions effective to provide a Formula (II) yield of at least about 75%, more preferably at least about 85%, and more preferably at least about 90%. In certain preferred embodiments a yield of about 95% or greater is achieved.

DETAILED DESCRIPTION OF PREFERRED EMBODIMENTS

One beneficial aspect of the present invention is that it enables the production of desirable fluroolefins, preferably C3 fluoroolefins, using relatively high conversion and high selectivity reactions. Furthermore, the present methods in certain preferred embodiments permit the production of the desirable fluoroolefins, either directly or indirectly, from relatively attractive starting materials. For example, 2-chloro, 2,3,3,3-tetrafluoropropane is a compound that may in certain embodiments be an advantageous starting material because such products are relatively easy to handle.

Preferably the Formula (I) compound is exposed to reaction conditions effective to produce a reaction product containing one or more of the desired fluorolefins, preferably one or more compounds of Formula (II). Although it is contemplated that the exposure step in certain embodiments may effectively be carried out in a single reaction stage and/or under a single set of reaction conditions, as mentioned above, it is preferred in many embodiments that the conversion step comprise a series of reaction stages or conditions. In one preferred aspect of the present invention, the conversion step comprises: (a) reacting a compound of Formula (I) which is not a compound of Formula (IAA), preferably a compound of Formula (IA), in a gas and/or liquid phase reaction in the presence of at least a first catalyst to produce at least one compound of Formula (IAA), such as a monochloro-trifluoro-propene, preferably HFO-1233xf; (b) reacting the at least one monochloro-trifluoro-propene compound, in a gas and/or liquid phase and preferably in the presence of at least a catalyst, preferably a second catalyst which is different than the first catalyst, to produce at least one compound of Formula (IB) and even more preferably Formula (IBB), such as monochloro-terafluoro-propane; and (c) reacting said compound of Formula (IB), in a gas and/or liquid phase, to produce the desired HFO, preferably HFO-1234yf. Each of the preferred reaction steps is described in detail below, with the headings being used for convenience but not necessarily by way of limitation.

I. Fluorination of the Compound of Formula I(A)

One preferred reaction step in accordance with the present invention may be described by those reactions in which the compound of Formula (IA) is fluorinated to produce a compound of Formula (IAA). In certain preferred embodiments, especially embodiments in which the compound of Formula (IA) comprises $C(X)_2\!=\!CClC(X)_3$, where each X is independently H or Cl, the present converting step comprises first reacting said compound(s) by fluorinating said compound(s), preferably with HF in a gas phase, to produce an HFO that is at least trifluorinated, such as HFO-1223xf. Preferably this gas phase reaction is at least partially catalyzed.

The preferred fluorination of the compound of Formula (IA) is preferably carried out under conditions effective to provide a Formula (IA) conversion of at least about 50%, more preferably at least about 75%, and even more preferably at least about 90%. In certain preferred embodiments the conversion is at least about 95%, and more preferably at least about 97%. Further in certain preferred embodiments, the conversion of the compound of Formula (IA) comprises reacting such compound under conditions effective to produce at least one compound of Formula (IAA), such as monochlorotrifluoropropene (preferably $CF_3CCl=CH_2$ (HFO-1233xf)) at a selectivity of at least about 50%, more preferably at least about 70%, more preferably at least about 80%, and even more preferably at least about 90%, with selectivities of about 95% or greater being achieved in certain embodiments.

In general, it is possible that the fluorination reaction step can be carried out in the liquid phase or in the gas phase, or in a combination of gas and liquid phases, and it is contemplated that the reaction can be carried out batch wise, continuous, or a combination of these.

For embodiments in which the reaction comprises a liquid phase reaction, the reaction can be catalytic or non-catalytic. Preferably, a catalytic process is used. Lewis acid catalyst, such as metal-halide catalysts, including antimony halides, tin halides, thallium halides, iron halides, and combinations of two or more of these, are preferred in certain embodiments. Metal chlorides and metal fluorides are particularly preferred. Examples of particularly preferred catalysts of this type include $SbCl_5$, $SbCl_3$, $SbF_5$, $SnCl_4$, $TiCl_4$, $FeCl_3$ and combinations of two or more of these.

In preferred gas phase fluorination of Formula (I) compounds, preferably Formula (IA) compounds, the reaction is at least partially a catalyzed reaction, and is preferably carried out on a continuous basis by introducing a stream containing the compound of Formula (I), preferably Formula (IA), into one or more reaction vessels, such as a tubular reactor. In certain preferred embodiments, the stream containing the compound of Formula (I), and preferably Formula (IA), is preheated to a temperature of from about 80° C. to about 400° C., more preferably from about 150° C. to about 400° C., and in certain embodiments preferably about 300° C., and introduced into a reaction vessel (preferably a tube reactor), which is maintained at the desired temperature, preferably from about 80° C. to about 700° C., more preferably from about 90° C. to about 600° C., even more preferably in certain embodiments from about 400° C. to about 600° C., more preferably from about 450° C. to about 600° C., where it is preferably contacted with catalyst and fluorinating agent, such as HF.

Preferably the vessel is comprised of materials which are resistant to corrosion as Hastelloy, Inconel, Monel and/or fluoropolymers linings.

Preferably the vessel contains catalyst, for example a fixed or fluid catalyst bed, packed with a suitable fluorination catalyst, with suitable means to ensure that the reaction mixture is maintained with the desired reaction temperature range.

Thus, it is contemplated that the fluorination reaction step may be preformed using a wide variety of process parameters and process conditions in view of the overall teachings contained herein. However, it is preferred in certain embodiments that this reaction step comprise a gas phase reaction, preferably in the presence of catalyst, and even more preferably a chromium-based catalyst (such as $Cr_2O_3$ catalyst), an iron-based catalyst (such as $FeCl_3$ on carbon (designated herein as $FeCl_3/C$ for convenience), and combinations of these. In preferred embodiments, the catalyst is a combination of the two aforementioned catalysts, where the reaction vessel contains in a first zone the chromium-based catalyst and in a second zone the iron-based catalyst. The temperature of the reaction in the chromium-based catalyst reaction is preferably kept at a temperature of from about 200° C. to about 600° C. and even more preferably from about 250° C. to about 500° C. The temperature of the reaction in the iron-based catalyst reaction zone is preferably kept at a temperature of from about 80° C. to about 300° C. and even more preferably from about 100° C. to about 250° C.

In general it is also contemplated that a wide variety of reaction pressures may be used for the fluorination reaction, depending again on relevant factors such as the specific catalyst being used and the most desired reaction product. The reaction pressure can be, for example, superatmospheric, atmospheric or under vacuum and in certain preferred embodiments is from about 1 to about 200 psia, and in certain embodiments from about 1 to about 120 psia.

In certain embodiments, an inert diluent gas, such as nitrogen, may be used in combination with the other reactor feed(s).

It is contemplated that the amount of catalyst use will vary depending on the particular parameters present in each embodiment.

II. Fluorination of the Compound of Formula I(AA)

The compound of Formula (IAA), preferably produced as described above, and then is preferably subject to further fluorination reaction(s) to produce a compound of Formula (IB), such as HCFC-244. Preferably this gas phase reaction is at least partially catalyzed.

The fluorination of the compound of Formula (IAA) is preferably carried out under conditions effective to provide a Formula (IAA) conversion of at least about 40%, more preferably at least about 50%, and even more preferably at least about 60%. Further in certain preferred embodiments, the conversion of the compound of Formula (IA) comprises reacting such compound under conditions effective to produce at least one monochlorotetrafluoropropane, preferably HCFC-244, at a selectivity of at least about 70%, more preferably at least about 80%, and even more preferably at least about 85%, with selectivities of about 90% or greater being achieved in certain embodiments.

In general, it is possible that this fluorination reaction step can be carried out in the liquid phase or in the gas phase, or in a combination of gas and liquid phases, and it is contemplated that the reaction can be carried out batch wise, continuous, or a combination of these.

For embodiments in which the reaction comprises a liquid phase reaction, the reaction can be catalytic or non-catalytic. Preferably, a catalytic process is used. Lewis acid catalyst, such as metal-halide catalysts, including antimony halides, tin halides, thallium halides, iron halides, and combinations of two or more of these, are preferred in certain embodiments. Metal chlorides and metal fluorides are particularly preferred. Examples of particularly preferred catalysts of this type include $SbCl_5$, $SbCl_3$, $SbF_5$, $SnCl_4$, $TiCl_4$, $FeCl_3$ and combinations of two or more of these.

In preferred gas phase fluorination of Formula (IAA) compounds, the reaction is at least partially a catalyzed reaction, and is preferably carried out on a continuous basis by introducing a stream containing the compound of Formula (IAA) into one or more reaction vessels, such as a tubular reactor. In certain preferred embodiments, the stream containing the compound of Formula (I), and preferably Formula (IAA), is preheated to a temperature of from about 50° C. to about 400° C., and in certain embodiments preferably about 80° C. In other embodiments, it is preferred that the stream containing the compound of Formula (I), and preferably Formula (IAA), is preheated to a temperature of from about 150° C. to about 400° C., preferably about 300° C. This steam, preferably after preheating, is then preferably introduced into a reaction vessel (preferably a tube reactor), which is maintained at the desired temperature, preferably from about 50° C. to about 250° C., more preferably from about 50° C. to about 150° C., where it is preferably contacted with catalyst and fluorinating agent, such as HF.

Preferably the vessel is comprised of materials which are resistant to corrosion as Hastelloy, Inconel, Monel and/or fluoropolymers linings.

Preferably the vessel contains catalyst, for example a fixed or fluid catalyst bed, packed with a suitable fluorination catalyst, with suitable means to ensure that the reaction mixture is maintained within about the desired reaction temperature range.

Thus, it is contemplated that the fluorination reaction step may be preformed using a wide variety of process parameters and process conditions in view of the overall teachings contained herein. However, it is preferred in certain embodiments that this reaction step comprise a gas phase reaction, preferably in the presence of catalyst, and even more preferably an Sb-based catalyst, such as catalyst which is about 50 wt % $SbCl_5$/C. Other catalysts which may be used include: from about 3 to about 6 wt % $FeCl_3$/C; $SbF_5$/C; about 20 wt % $SnCl_4$/C; about 23 wt % $TiCl_4$/C; and activated carbon. Preferably the catalyst comprises $Cl_2$ and HF pre-treated $SbCl_5$/C.

In general it is also contemplated that a wide variety of reaction pressures may be used for the fluorination reaction, depending again on relevant factors such as the specific catalyst being used and the most desired reaction product. The reaction pressure can be, for example, superatmospheric, atmospheric or under vacuum and in certain preferred embodiments is from about 1 to about 200 psia, more preferably in certain embodiments from about 1 to about 120 psia.

In certain embodiments, an inert diluent gas, such as nitrogen, may be used in combination with the other reactor feed(s).

It is contemplated that the amount of catalyst use will vary depending on the particular parameters present in each embodiment.

III. Dehydrohalogenation of Formula (IB)

One preferred reaction step in accordance with the present invention may be described by those reactions in which the compound of Formula (IB) is dehydrohalogenated to produce a compound of Formula (II). In certain preferred embodiments, the stream containing the compound of Formula (IB), and preferably Formula (IBB) is preheated to a temperature of from about 150° C. to about 400° C., preferably about 350° C., and introduced into a reaction vessel, which is maintained at about the desired temperature, preferably from about 200° C. to about 700° C., more preferably from about 300° C. to about 700° C., more preferably from about 300° C. to about 450° C., and more preferably in certain embodiments from about 350° C. to about 450° C.

Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to about the desired reaction temperature.

Thus, it is contemplated that the dehydrohalogenation reaction step may be preformed using a wide variety of process parameters and process conditions in view of the overall teachings contained herein. However, it is preferred in certain embodiments that this reaction step comprise a gas phase reaction, preferably in the presence of catalyst, and even more preferably a carbon- and/or metal-based catalyst, preferably activated carbon, a nickel-based catalyst (such as Ni-mesh) and combinations of these. Other catalysts and catalyst supports may be used, including palladium on carbon, palladium-based catalyst (including palladium on aluminum oxides), and it is expected that many other catalysts may be used depending on the requirements of particular embodiments in view of the teachings contained herein. Of course, two or more any of these catalysts, or other catalysts not named here, may be used in combination.

The gas phase dehydrohalogenation reaction may be conducted, for example, by introducing a gaseous form of a compound of Formula (IB) into a suitable reaction vessel or reactor. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to about the desired reaction temperature.

While it is contemplated that a wide variety of reaction temperatures may be used, depending on relevant factors such as the catalyst being used and the most desired reaction product, it is generally preferred that the reaction temperature for the dehydrohalogentation step is from about 200° C. to about 800° C., more preferably from about 400° C. to about 800° C., and even more preferably from about 400° C. to about 500° C., and more preferably in certain embodiments from about 300° C. to about 500° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum, and in certain preferred embodiments is from about 1 to about 200 psia, and even more preferably in certain embodiments from about 1 to about 120 psia.

In certain embodiments, an inert diluent gas, such as nitrogen, may be used in combination with the other reactor feed(s). When such a diluent is used, it is generally preferred that the compound of Formula (I), preferably Formula (IB), comprise from about 50% to greater than 99% by weight based on the combined weight of diluent and Formula (I) compound.

It is contemplated that the amount of catalyst use will vary depending on the particular parameters present in each embodiment.

Preferably in such dehydrofluorination embodiments as described in this section, the conversion of the Formula (IB) compound is at least about 60%, more preferably at least about 75%, and even more preferably at least about 90%. Preferably in such embodiments, the selectivity to compound of Formula (II), preferably HFO-1234yf, is at least about 50%, more preferably at least about 70% and more preferably at least about 80%.

EXAMPLES

Additional features of the present invention are provided in the following examples, which should not be construed as limiting the claims in any way.

Example 1

Preparation of $CH_2$=$CClCH_2Cl$(2,3-Dichloro-1-propene) from $CH_2ClCHClCH_2Cl$ About 8500 grams of 1,2,3-trichloropropane and about 88.0 grams Aliquat 336 were charged into a 30 liter glass vessel, equipped with TEFLON® shaft and stir blades, heated with internal TEFLON® coated copper coils and refrigerant/ heating circulation bath and refrigerated condenser. The mixture was then heated to about 73° C. with medium speed agitation. At this temperature, about 10,000 grams of 25 wt % NaOH/H2O solution is added into the reactor from a separate container over a 2 hour period of time. The pH was kept at about 14. After addition, the reaction progress was monitored by GC and GC/MS. The conversion of 1,2,3-trichloropropane was about 97.5% and the selectivity to $CH_2=CClCH_2Cl$ was about 95.4%. After the stipulated reaction time, the mixture was cooled and about 4.0 liters of distilled and ionized water was added into the mixture. The mixture was stirred for about 10 minutes and allowed to separate. The lower layer product (boiling point of about 92.5° C.) was drained and distilled to substantially isolate and purify product. The crude yield before distillation was about 6408 grams (GC purity of about 93%).

Example 2

Preparation of $HCCl_2CCl_2CH_2Cl$ from $CH_2=CClCH_2Cl$

Chlorine was bubbled into about 82.4 g of 2,3-dichloropropene at about 10 to about 30° C. with the aid of ice bath cooling until a pale yellow color persisted for about 45 minutes. The crude product in an amount of about 130.4 g, consisted of about 93.6% $CH_2ClCCl_2CH_2Cl$ and about 2.6% 2,3-dichloropropene.

Five hundred grams of $CH_2ClCCl_2CH_2Cl$ was charged into a photoreactor. The jacket for the reactor as well as the jacket for the 450 W UV lamp were cooled to about 15° C. using a circulating cooling bath. A total of about 150 g of chlorine was bubbled into the organic liquid over a period of about 2 hours. The crude product weighed about 591 g. GC analysis indicated a conversion of about 54.4% and selectivity for the desired $HCCl_2CCl_2CH_2Cl$ of about 87%. Distillation provided $HCCl_2CCl_2CH_2Cl$ in 99% purity.

Example 3

Preparation of $CCl_2=CClCH_2Cl$ from $HCCl_2CCl_2CH_2Cl$

Aliquat-336® (about 0.26 g) and about 24.8 g of $HCCl_2CCl_2CH_2Cl$ were stirred rapidly at room temperature while adding about 20 g of 25% aqueous NaOH over 19 minutes. Stirring was continued overnight before adding 30 mL water and allowing the phases to separate. The lower organic phase, in an amount of about 19.8 g, was about 97.5% pure $CCl_2=CClCH_2Cl$ by GC analysis (96% yield). Prior to fluorination, it was distilled (bp about 69 to about 72° C. at about 30 mm Hg) to remove any phase transfer catalyst. H NMR: δ 4.41 (s) ppm.

Example 4

Selective Catalyzed-transformation of $CCl_2=CClCH_2Cl$ to $CF_3CCl=CH_2$ (HFO-1233xf) in Gas-Phase An 22-inch long and ½-inch diameter Monel pipe gas-phase reactor is charged with about 120 cc of a catalyst or a mixture of two catalysts. In case of a mixture, $Cr_2O_3$ catalyst is kept at the bottom zone of the reactor at a constant temperature of about 270° C.-500° C. and the other catalyst, such as $FeCl_3/C$, is kept at the middle and the top zone of the reactor at a constant temperature of about 120° C.-220° C. The reactor is mounted inside a heater with three zones (top, middle, and bottom). The reactor temperature is read by custom-made-5-point thermocouples kept inside at the middle of the reactor. The bottom of the reactor is connected to a pre-heater, which is kept at 300° C. by electrical heating. The liquid-HF is fed from a cylinder into the pre-heater through a needle valve, liquid mass-flow meter, and a research control valve at a constant flow of about 1 to about 1000 grams pre hour (g/h). The HF cylinder is kept at a constant pressure of 45 psig by applying anhydrous $N_2$ gas pressure into the cylinder head space. About 10 to about 1000 g/h of $CCl_2=CClCH_2Cl$ is fed as a liquid through a dip tube from a cylinder under about 45 psig of $N_2$ pressure. The organic flows from the dip tube to the preheater (kept at about 250° C.) through a needle valve, liquid mass-flow meter, and a research control valve at a constant flow of 1-1000 g/h. The organic is also fed as a gas while heating the cylinder containing organic at about 220° C. The gas coming out of the cylinder is passed through a needle valve and a mass flow controller into the preheater. The organic line from the cylinder to the pre-heater is kept at about 200° C. by wrapping with constant temperature heat trace and electrical heating elements. All feed cylinders are mounted on scales to monitor their weight by difference. The catalysts are dried at the reaction temperature over a period of about 8 hours and then pretreated with about 50 g/h of HF under atmospheric pressure over a period of about 6 hours and then under 50 psig HF pressure over another period of about 6 hours before contacting with organic feed containing $CCl_2=CClCH_2Cl$. The reactions are run at a constant reactor pressure of about 0 to about 150 psig by controlling the flow of reactor exit gases by another research control valve. The gases exiting reactor are analyzed by on-line GC and GC/MS connected through a hotbox valve arrangement to prevent condensation. The conversion of $CCl_2=CClCH_2Cl$ is about 70 to about 100% and the selectivity to 1233xf is about 80% to about 95%, respectively. The product is collected by flowing the reactor exit gases through a scrubber solution comprising about 20 wt % to about 60 wt %. KOH in water and then trapping the exit gases from the scrubber into a cylinder kept in dry ice or liquid $N_2$. The product, 1233xf is then substantially isolated by distillation. The results are tabulated in Table 1.

TABLE 1

Transformation of $CCl_2=CClCH_2Cl$ to $CF_3CCl=CH_2$ ($CCl_2=CClCH_2Cl + 3HF \rightarrow CF_3CCl=CH_2 + 3HCl$)

| # | Catalyst | T, °C. | HF flow, g/h | $CCl_2=CClCH_2Cl$ flow, g/h | % Conv of $CCl_2=CClCH_2Cl$ | % Sel to 1233xf |
|---|---|---|---|---|---|---|
| 1 | 10% v/v $Cr_2O_3$-90% v/v $FeCl_3/C$ | 350/150 | 50 | 12 | 79 | 81 |
| 2 | 20% v/v $Cr_2O_3$-80% v/v $FeCl_3/C$ | 350/150 | 50 | 12 | 83 | 86 |

TABLE 1-continued

Transformation of $CCl_2=CClCH_2Cl$ to
$CF_3CCl=CH_2$ ($CCl_2=CClCH_2Cl + 3HF \rightarrow CF_3CCl=CH_2 + 3HCl$)

| # | Catalyst | T, °C. | HF flow, g/h | $CCl_2=CClCH_2Cl$ flow, g/h | % Conv of $CCl_2=CClCH_2Cl$ | % Sel to 1233xf |
|---|---|---|---|---|---|---|
| 3 | 30% v/v $Cr_2O_3$-70% v/v $FeCl_3$/C | 350/150 | 50 | 12 | 89 | 96 |
| 4 | 30% v/v $Cr_2O_3$-70% v/v $FeCl_3$/C | 350/150 | 70 | 12 | 79 | 93 |
| 5 | 30% v/v $Cr_2O_3$-70% v/v $FeCl_3$/C | 345/170 | 50 | 25 | 85 | 90 |
| 6 | $Cr_2O_3$ | 350 | 50 | 20 | 90 | 93 |
| 7 | $FeCl_3$/C | 150 | 50 | 20 | 74 | 39 |
| 8 | $SbCl_5$/C | 150 | 50 | 20 | 81 | 52 |

Reaction conditions: Catalyst used (total) 120 cc; pressure, 1.5 psig;

Examples 5A and 5B

Liquid-phase Catalytic Fluorination of $CF_3CCl=CH_2$ (1233xf) with HF to $CF_3CFClCH_3$ (244bb)

Example 5A

About 327 grams of HF, about 50 grams 1233xf, and about 75 grams $SbCl_5$ were charged into a 1-L autoclave. The reaction mixture was stirred at a temperature of about 80° C. for about 3 hours under about 620 psig of pressure. After the reaction, the reactor was cooled to about 0° C. and about 300 ml water was then added slowly into the autoclave over a period of about 45 min. After complete addition of water under stirring, the reactor was cooled to room temperature and then the overhead gases were transferred to another collecting cylinder. The yield of $CF_3CFClCH_3$ was about 90% at a 1233xf conversion level of about 98%. The other major by-products were $CF_3CF_2CH_3$ (2%), and an unidentified isomer of a C4 compound of the general formula, $C_4H_3Cl_3F_4$ (8%).

Example 5B

About 327 grams HF, about 50 grams 1233xf, and about 75 grams $SbCl_5$ were charged into a 1-L autoclave. The reaction mixture was stirred at 80° C. for about 3 hours under about 625 psig of pressure. After the reaction, the reactor was cooled to about 45° C. and then the overhead gas mixture was passed through a well dried KF, NaF, or $Al_2O_3$ (350 g) packed column kept at about 80° C. to strip off HF from the gas stream. The gases coming out of the column are collected in a cylinder kept in dry ice (−70° C.) bath. The yield of $CF_3CFClCH_3$ was 87% at a 1233xf conversion level of 93%. The other major by-products were $CF_3CF_2CH_3$ (1%), and an unidentified isomer of a C4 compound of the general formula, $C_4H_3Cl_3F_4$ (7%). The product, $CF_3CFClCH_3$ was isolated by distillation with 98% purity.

Example 6

Gas-phase Catalytic Fluorination of $CF_3CCl=CH_2$ (1233xf) with HF to $CF_3CFClCH_3$ (244bb)

A 22-inch (½-inch diameter) Monel tube gas phase reactor was charged with about 120 cc of a catalyst. The reactor was mounted inside a heater with three zones (top, middle and bottom). The reactor temperature was read by a custom made 5-point thermocouple kept at the middle inside of the reactor. The inlet of the reactor was connected to a pre-heater, which was kept at about 300° C. by electrical heating. Organic (1233xf) was fed from a cylinder kept at 70° C. through a regulator, needle valve, and a gas mass-flow-meter. The organic line to the pre-heater was heat traced and kept at a constant temperature of about 73° C. by electrical heating to avoid condensation. $N_2$ was used as a diluent in some cases and fed from a cylinder through a regulator and a mass flow controller into the pre-heater. All feed cylinders were mounted on scales to monitor their weight by difference. The reactions were run at a constant reactor pressure of from about 0 to about 100 psig by controlling the flow of reactor exit gases by another research control valve. The gas mixtures exiting reactor was analyzed by on-line GC and GC/MS connected through a hotbox valve arrangements to prevent condensation. The conversion of 1233xf was from about 50% to about 65% and the selectivity to 244 isomer ($CF_3CFClCH_3$) was from about 90% to about 93% depending on the reaction conditions using 120 cc of 50 wt % $SbCl_5$/C as the catalyst at about 65° C. to about −85° C. with a HF flow of about 50 g/h and organic flow of about 15 g/h. No $CF_3CF_2CH_3$ was observed under the reaction conditions. The catalyst is pretreated at first with 50 g/h HF at about 65° C. for about 2 hours and then with about 50 g/h HF and about 200 sccm of $Cl_2$ at about 65° C. for about 4 hours. After pre-treatment, about 50 sccm of $N_2$ is flows over a period of about 40 minutes through the catalyst bed to sweep free chlorine from the catalyst surface prior to interacting with the organic feed (1233xf). Pretreatment is considered important to many embodiments of the invention. The products were collected by flowing the reactor exit gases through a 20-60 wt % aqueous KOH scrubber solution and then trapping the exit gases from the scrubber into a cylinder kept in dry ice or liquid $N_2$. The products were then isolated by distillation. About 50 wt % $SbCl_5$/C, about 3 to about 6 wt % $FeCl_3$/C, 20 wt % $SnCl_4$/C, and about 23 wt % $TiCl_4$/C, using 4 different kind of activated carbon such as Shiro saga, Calgon, Norit, and Aldrich were used as the catalyst at from about 60 to about 150° C. Among all the catalysts used for this reaction, $Cl_2$ and HF pre-treated $SbCl_5$/C was found to be generally preferred in terms of activity. The results using $SbCl_5$ as the catalyst are shown in Table 2.

TABLE 2

Catalyzed-gas-phase transformation of $CF_3CCl=CH_2$ to $CF_3CFClCH_3$

| # | Cat | T, °C. | Conv. of $CF_3CCl=CH_2$ (1233xf) | Sel. to $CF_3CFClCH_3$ |
|---|---|---|---|---|
| 1 | 10 wt % $SbCl_5$/C | 60 | 15 | 100 |
| 2 | 20 wt % $SbCl_5$/C | 60 | 21 | 98 |
| 3 | 30 wt % $SbCl_5$/C | 60 | 32 | 98 |

TABLE 2-continued

Catalyzed-gas-phase transformation
of $CF_3CCl=CH_2$ to $CF_3CFClCH_3$

| # | Cat | T, °C. | Conv. of $CF_3CCl=CH_2$ (1233xf) | Sel. to $CF_3CFClCH_3$ |
|---|---|---|---|---|
| 4 | 50 wt % $SbCl_5$/C | 60 | 55 | 97 |
| 5 | 50 wt % $SbCl_5$/C | 80 | 62 | 93 |
| 6 | 50 wt % $SbCl_5$/C | 100 | 56 | 87 |
| 7 | 60 wt % $SbCl_5$/C | 60 | 59 | 91 |
| 8 | 50 wt % $SbCl_5$/ NORIT RFC 3 Activated Carbon | 60 | 34 | 92 |
| 9 | 50 wt % $SbCl_5$/ Shiro Saga Activated Carbon | 60 | 56 | 96 |
| 10 | 50 wt % $SbCl_5$/ Aldrich Activated Carbon | 60 | 57 | 94 |

Reaction conditions: 1233xf flow, 150 sccm; HF flow 50 g/h; pressure, 2.5-5.3 psig; in 1-5 reactions Calgon activated carbon is used as the catalyst support; catalyst, 120 cc. All catalysts are pre-treated with $Cl_2$ and HF prior to contacting with 1233xf.

Example 7

Conversion of $CF_3CFClCH_3$ to $CF_3CF=CH_2$ in Gas-phase

A 22-inch (½-inch diameter) Monel tube gas phase reactor was charged with 120 cc of catalyst. The reactor was mounted inside a heater with three zones (top, middle and bottom). The reactor temperature was read by custom made 5-point thermocouples kept at the middle inside of the reactor. The inlet of the reactor was connected to a pre-heater, which was kept at about 300° C. by electrical heating. Organic ($CF_3CFClCH_3$) was fed from a cylinder kept at about 65° C. through a regulator, needle valve, and a gas mass-flow-meter. The organic line to the pre-heater was heat traced and kept at a constant temperature of from about 65° C. to about 70° C. by electrical heating to avoid condensation. The feed cylinder was mounted on scales to monitor their weight by difference. The reactions were run at a constant reactor pressure of from about 0 to about 100 psig by controlling the flow of reactor exit gases by another research control valve. The gas mixture exiting reactor was analyzed by on-line GC and GC/MS connected through a hotbox valve arrangement to prevent condensation. The conversion of $CF_3CFClCH_3$ was almost 98% and the selectivity to HFO-1234yf was from about 69% to about 86% depending on the reaction conditions. The products were collected by flowing the reactor exit gases through a about 20 wt % to about 60 wt % of aqueous KOH scrubber solution and then trapping the exit gases from the scrubber into a cylinder kept in dry ice or liquid $N_2$. The products were then isolated by distillation. Results are tabulated in Table 3.

TABLE 3

Catalyzed-transformation of $CF_3CFClCH_3$ to HFO-1234yf

| # | Cat | T, °C. | Flow rate, $CF_3CFClCH_3$ (244 isomer) sccm | Conversion of 244 | 1234yf (Sel. %) |
|---|---|---|---|---|---|
| 1 | A | 400 | 150 | 100 | 46 |
| 2 | B | 400 | 150 | 96 | 63 |
| 3 | C | 400 | 100 | 100 | 64 |
| 4 | D | 400 | 100 | 99 | 93 |
| 5 | D | 400 | 150 | 92 | 89 |
| 6 | E | 400 | 100 | 96 | 56 |
| 7 | F | 400 | 100 | 87 | 51 |
| 8 | G | 400 | 100 | 100 | 37 |

Reaction conditions: pressure, 2.5-5.3 psig; catalyst, 100 cc, A is NORIT RFC 3; B is Shiro-Saga activated carbon; C is Aldrich activated carbon; D is Calgon activated carbon; activated carbon; E is 0.5 wt % Pd/C; F is 0.5 wt % Pt/C; G is Ni-mesh; Organic cylinder temperature-65° C.; $CF_3CFClCH_3$ (244) line to the preheater-60° C.; Preheater, 350° C.; P-5 psig.

Example 8

Selective Catalyzed-transformation of $CCl_3CCl=CH_2$ to $CF_3CCl=CH_2$ (HFO-1233xf) in Gas-Phase A 22-inch long and ½-inch diameter Monel pipe gas phase reactor was charged with 120 cc of a catalyst or a mixture of two catalysts. In case of a mixture, $Cr_2O_3$ catalyst is kept at the bottom zone of the reactor at a substantially constant temperature of from about 270° C. to about 500° C. and the other catalyst, such as $FeCl_3$/C is kept at the middle and the top zone of the reactor at a substantially constant temperature of from about 120° C. to about 220° C. The reactor was mounted inside a heater with three zones (top, middle, and bottom). The reactor temperature was read by custom-made-5-point thermocouples kept inside at the middle of the reactor. The bottom of the reactor was connected to a pre-heater, which was kept at about 300° C. by electrical heating. The liquid-HF was fed from a cylinder into the pre-heater through a needle valve, liquid mass-flow meter, and a research control valve at a substantially constant flow of from about 1 to about 1000 g/h. The HF cylinder was kept at a substantially constant pressure of about 45 psig by applying anhydrous $N_2$ gas pressure into the cylinder head space. A feed rate of from about 10 g/h to about 1000 g/h of $CCl_3CCl=CH_2$ was fed as a liquid through a dip tube from a cylinder under about 45 psig of $N_2$ pressure. The organic was flown from the dip tube to the pre-heater (kept at about 250° C.) through needle valve, liquid mass-flow meter, and a research control valve at a substantially constant flow of from about 1 to about 1000 g/h. The organic is also fed as a gas while heating the cylinder containing organic at about 220° C. The gas effluent from the cylinder is passed through a needle valve and a mass flow controller into the pre-heater. The organic line from the cylinder to the pre-heater was kept at about 200° C. by wrapping with constant temperature heat trace and electrical heating elements. All feed cylinders were mounted on scales to monitor their weight by difference. The catalysts were dried at the reaction temperature over a period of about 8 hours and then pretreated with about 50 g/h of HF under atmospheric pressure over a 6 hour period and then under about 50 psig HF pressure over a 6 hour period before contacting with organic feed, $CCl_3CCl=CH_2$. The reactions were run at a substantially constant reactor pressure ranging from about 0 to about 150 psig by controlling the flow of reactor exit gases by another research control valve. Those gases exiting reactor were analyzed by on-line GC and GC/MS connected through a hotbox valve arrangements to prevent condensation. The conversion of $CCl_3CCl=CH_2$ was in a range of from about 90% to about 100% and the selectivity to $CF_3CCl=CH_2$ (1233xf) was about 79%. The effluent contained in addition HFO-1243zf in an amount of about 7.7%, 1232-isomer in an amount of about 1.3%, and 1223 in an amount of about 0.8%, and an unidentified byproduct. The product was collected by flowing the reactor exit gases through a 20-60 wt % aq. KOH scrubber solution and then trapping the exit gases from the scrubber into a cylinder kept in dry ice or liquid $N_2$. The product, 1233xf was then substantially isolated by distillation. Using only $Cr_2O_3$ catalyst, a selectivity of about 68% to 1233xf at a conversion level of about 79% was achieved.

Examples 9A-9D

Direct Liquid-phase Catalytic Fluorination of $CCl_3CCl\!=\!CH_2$ with HF to $CF_3CFClCH_3$ (244-isomer)

Example 9A

About 327 grams HF, about 50 grams $CCl_3CCl\!=\!CH_2$, and about 75 grams $SbCl_5$ were charged into a 1-L autoclave. The reaction mixture was stirred at about 80° C. for about 3 hours under about 610 psig of pressure. After the reaction, the reactor was cooled to about 40° C. and about 300 ml water was then added slowly into the autoclave over a period of about 45 min. After complete addition of water under stirring, the reactor was cooled to about room temperature and then the overhead gases were transferred to another collecting cylinder. The yield of $CF_3CFClCH_3$ was about 89% at a $CCl_3CCl\!=\!CH_2$ conversion level of about 88%. The other major by-products were $CF_3CF_2CH_3$ (2%), and an unidentified isomer of a C4 compound of the general formula, $C_4H_3Cl_3F_4$ (8%).

Example 9B

About 327 grams HF, about 50 grams $CCl_3CCl\!=\!CH_2$, and about 75 grams $SbCl_5$ were charged into a 1-L autoclave. The reaction mixture was stirred at about 100° C. for about 3 hours under about 685 psig of pressure. After the reaction, the reactor was cooled to about 40° C. and about 300 ml water was then added slowly into the autoclave over a period of about 45 minutes. After complete addition of water under stirring, the reactor was cooled to room temperature and then the overhead gases were transferred to another collecting cylinder. The yield of $CF_3CFClCH_3$ was about 78% at a $CCl_3CCl\!=\!CH_2$ conversion level of about 100%. The other major by-products were $CF_3CF_2CH_3$ (about 4%), and an unidentified isomer of a C4 compound of the general formula, $C_4H_3Cl_3F_4$ (about 13%).

Example 9C

About 327 grams HF, about 50 grams $CCl_3CCl\!=\!CH_2$, and about 75 grams SbCl5 were charged into a 1-L autoclave. The reaction mixture was stirred at about 125° C. for about 6 hours under about 825 psig of pressure. After the reaction, the reactor was cooled to about 40° C. and about 300 ml water was then added slowly into the autoclave over a period of about 45 min. After complete addition of water under stirring, the reactor was cooled to about room temperature and then the overhead gases were transferred to another collecting cylinder. The major products were $CF_3CF_2CH_3$ (about 53%) and $CF_3CFClCH_3$ (about 25%) at a $CCl_3CCl\!=\!CH_2$ conversion level of about 100%. The other major by-products were and unidentified isomer of a C4 compound of the general formula, $C_4H_3Cl_3F_4$ (8%) and tar.

Example 9D

About 327 grams HF, about 50 grams $CCl_3CCl\!=\!CH_2$, and about 75 g $SbCl_5$ were charged into a 1-L autoclave. The reaction mixture was stirred at about 150° C. for about 6 hours under about 825 psig of pressure. After the reaction, the reactor was cooled to about 40° C. and about 300 ml water was then added slowly into the autoclave over a period of about 45 minutes. After complete addition of water under stirring, the reactor was cooled to about room temperature and then the overhead gases were transferred to another collecting cylinder. The major products were $CF_3CF_2CH_3$ (about 57%) and $CF_3CFClCH_3$ (about 15%) at a $CCl_3CCl\!=\!CH_2$ conversion level of about 100%. The other major by-products were and unidentified isomer of a C4 compound of the general formula, $C_4H_3Cl_3F_4$ (about 11%) and tar.

Example 10

Catalytic Conversion of $CF_3CF_2CH_3$ to $CF_3CF\!=\!CH_2$

A 22-inch (½-inch diameter) Monel tube gas phase reactor was charged with 120 cc of a catalyst. The reactor was mounted inside a heater with three zones (top, middle and bottom). The reactor temperature was read by custom made 5-point thermocouples kept at the middle inside of the reactor. The inlet of the reactor was connected to a pre-heater, which was kept at about 300° C. by electrical heating. Organic material (245 cb) was fed from a cylinder kept at about 65° C. through a regulator, needle valve, and a gas mass-flow-meter. The organic line to the pre-heater was heat traced and kept at a substantially constant temperature in a range of from about 65° C. to about 70° C. by electrical heating to avoid condensation. The feed cylinder was mounted on a scale to monitor its weight by difference. The reactions were run at a substantially constant reactor pressure of from about 0 to about 100 psig by controlling the flow of reactor exit gases by another research control valve. The gas mixtures exiting reactor was analyzed by on-line GC and GC/MS connected through a hotbox valve arrangements to prevent condensation. The conversion of 245 cb was in the range of from about 30% to about 70% and the selectivity to 1234yf was in the range of from about 90% 5 o about 100% depending on the reaction conditions. The products were collected by flowing the reactor exit gases through a 20-60-wt % of aq. KOH scrubber solution and then trapping the exit gases from the scrubber into a cylinder kept in dry ice or liquid $N_2$. The products were then substantially isolated by distillation. Results are tabulated in Table 4.

TABLE 4

Transformation of $CF_3CF_2CH_3$ to 1234yf

| # | Cat | T, °C. | $H_2$, sccm | $CF_3CF_2CH_3$ (245cb) sccm | Conversion of 245cb, % | 1234yf (Sel. %) |
|---|-----|--------|-------------|------------------------------|-------------------------|-----------------|
| 1 | A   | 575    | 0           | 65                           | 79                      | 63              |
| 2 | B   | 575    | 0           | 68                           | 82                      | 57              |
| 3 | C   | 575    | 0           | 73                           | 73                      | 61              |
| 4 | D   | 575    | 0           | 68                           | 84                      | 59              |
| 5 | D   | 575    | 20          | 68                           | 89                      | 73              |
| 6 | E   | 550    | 0           | 69                           | 92                      | 53              |
| 7 | F   | 550    | 0           | 67                           | 93                      | 33              |
| 8 | G   | 550    | 0           | 69                           | 73                      | 46              |

Reaction conditions: pressure, 2.5-5.3 psig; catalyst, 100 cc, A is NORIT RFC 3; B is Shiro-Saga activated carbon; C is Aldrich activated carbon; D is Calgon activated carbon; E is 0.5 wt % Pd/C; F is 0.5 wt % Pt/C; G is Ni-mesh; Organic cylinder temperature is about 65° C.; $CF_3CF_2CH_3$ (245 cb) line to the preheater is maintained at about 50° C.; preheater temperature is maintained at about 350° C.; $N_2$ flow is not used; pressure is maintained at about 3 psig.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting.

What is claimed is:

1. A method for producing fluorinated organic compounds comprising fluorinating at least one compound of Formula (IA)

$$C(X)_2=CClC(X)_3 \quad (IA)$$

to at least one compound of Formula (IB)

$$C(X)_3CClYC(X)_3 \quad (IB)$$

and dehydrohalogenating said at least one compound of Formula (IB) to at least one compound of Formula (II)

$$CF_3CF=CHZ \quad (II)$$

where each X, Y, and Z is independently H, F, Cl, I or Br.

2. The method of claim 1 wherein said at least one compound of Formula (IA) comprises a compound wherein each X is independently H or Cl, and Z is H.

3. The method of claim 1 wherein Z in said compound of Formula (II) is H.

4. The method of claim 1 wherein said at least one compound of Formula (IA) comprises at least one tetrachloropropene.

5. The method of claim 1 wherein said at least one compound of Formula (IA) comprises at least one tetrachloropropene.

6. The method of claim 1 wherein said at least one compound of Formula (IA) comprises $CH_2=CClCCl_3$.

7. The method of claim 1 wherein said at least one compound of Formula (IA) comprises $CCl_2=CClCH_2Cl$.

8. The method of claim 1 wherein said at least one compound of Formula (IA) comprises $CHCl=CClCCl_2H$.

9. The method of claim 1 wherein said at least one compound of Formula (IA) is selected from the group consisting of $CH_2=CClCCl_3$, $CCl_2=CClCH_2Cl$, $CHCl=CClCCl_2H$, and combinations of these.

10. The method of claim 1 wherein said at least one compound of Formula (IA) comprises a compound wherein the terminal saturated carbon has three (3) F substituents.

11. The method of claim 1 wherein said at least one compound of Formula (IA) comprises a compound Formula (IAA):

$$C(X)_2=CClCF_3 \quad (IAA)$$

wherein X is as identified in claim 1.

12. The method of claim 11 wherein each X in said compound of Formula (IAA) is independently H or Cl.

13. The method of claim 1 wherein said at least one compound of Formula (IA) comprises at least one trifluoropropene.

14. The method of claim 13 wherein said at least one trifluoropropene comprises $CH_2=CClCF_3$ (HCFC-1233xf).

15. The method of claim 1 wherein said fluorinating step comprises fluorinating at least said Formula (IA) compound to a compound of Formula (IAA)

$$C(X)_2=CClCF_3 \quad (IAA)$$

and then fluorinating said compound of Formula (IAA) to a compound of Formula (IB)

$$C(X)_3CClYC(X)_3 \quad (IB)$$

wherein X and Y are each as identified in claim 1.

16. The method of claim 15 wherein said compound of Formula (II) comprises at least one compound in which Z is H.

17. The method of claim 15 wherein said compound of Formula (IAA) comprises $CF_3CCl=CH_2$ (HCFC-1233xf) and is fluorinated under conditions effective to produce at least one monochloro-tetrafluoro-propane in accordance with Formula (IB).

18. The method of claim 17 wherein said monochloro-tetrafluoro-propane in accordance with Formula (IB) comprises $CF_3CFClCH_3$ (HFC-244bb).

19. The method of claim 18 wherein said $CF_3CFClCH_3$ (HFC-244bb) is dehydrohalogenated under reaction conditions effective to produce at least one compound in accordance with Formula (II) wherein Z is H.

20. The method of claim 19 wherein said at least one compound in accordance with Formula (II) comprises HFO-1234yf.

21. The method of claim 19 wherein said dehydrohalogenated step comprises at least one gas phase catalytic reaction.

22. The method of claim 1 wherein said fluorinating step comprises at least one gas phase catalytic reaction.

23. The method of claim 1 wherein said fluorinating step comprises exposing the compound of Formula (IA) to one or more sets of reaction conditions effective to produce at least one compound in accordance with Formula (II).

24. The method of claim 1 wherein said fluorinating step comprises reacting said at least one compound of Formula (IA) under conditions effective to produce at least one chlorofluoropropane.

25. The method of claim 24 wherein said at least one chlorofluoropropane is a compound in accordance with Formula (IBB):

$$CF_3CClFC(X)_3 \quad (IBB)$$

where each X is independently F, Cl or H.

26. The method of claim 25 wherein at least one of said X in Formula (IBB) is H.

27. The method of claim 26 wherein all three X in Formula (IBB) are H.

28. The method of claim 1 wherein said Formula (IB) compound has at least two chlorines on one terminal carbon and at least two hydrogen atoms on the other terminal carbon.

29. The method of claim 1 wherein said at least one compound of Formula (IB) comprises at least one propane having at least four chlorine substituents.

30. The method of claim 29 wherein said at least one compound of Formula (IB) comprises at least one propane having at least five chlorine substituents.

31. The method of claim 29 wherein said at least one compound of Formula (IB) is selected from the group consisting of $CH_2ClCHClCCl_3$, $CHCl_2CCl_2CH_2Cl$, $CHCl_2CHClCHCl_2$, and combinations thereof.

32. The method of claim 1 wherein said at least one compound of Formula (IB) comprises 1,1,1,2-tetrafluoro-2-chloropropane or 1-chloro-1,3,3,3-tetrafluoropropane.

33. A method for producing fluorinated organic compounds comprising dehydrohalogenating at least one compound of Formula (IB):

$$C(X)_3CCLYC(X)_3 \quad (IB)$$

to at least one compound of Formula (II):

$$CF_3CF=CHZ$$

wherein each X and Y are independently H or Cl, and Z is H, F, Cl, I or Br.

34. The method of claim 33 wherein said Formula (IB) compound has at least two chlorines on one terminal carbon and at least two hydrogen atoms on the other terminal carbon.

35. The method of claim 33 wherein said at least one compound of Formula (IB) comprises at least one propane having at least four chlorine substituents.

36. The method of claim 35 wherein said at least one compound of Formula (IB) comprises at least one propane having at least five chlorine substituents.

37. The method of claim 36 wherein said at least one compound of Formula (IB) comprises $CH_2ClCHClCCl_3$.

38. The method of claim 36 wherein said at least one compound of Formula (IB) comprises $CHCl_2CCl_2CH_2Cl$.

39. The method of claim 36 wherein said at least one compound of Formula (IB) comprises $CHCl_2CHClCHCl_2$.

40. The method of claim 36 wherein said at least one compound of Formula (IB) comprises at least one propane selected from the group consisting of $CH_2ClCHClCCl_3$, $CHCl_2CCl_2CH_2Cl$, $CHCl_2CHClCHCl_2$, and combinations thereof.

41. A method for producing fluorinated organic compounds comprising fluorinating at least one compound of Formula (IA)

$$C(X)_2{=}CClC(X)_3 \qquad (IA)$$

to at least one compound of Formula (IAA)

$$C(X)_2{=}CClCF_3 \qquad (IAA);$$

fluorinating said at least one compound of Formula (IAA) to at least one compound of Formula (IB)

$$C(X)_3CClYC(X)_3; \text{ and}$$

dehydrohalogenating said at least one compound of Formula (IB) to at least one compound of Formula (II)

$$CF_3CF{=}CHZ \qquad (II)$$

where each X, Y, and Z is independently H, F, Cl, I or Br.

* * * * *